(12) United States Patent
Driemel

(10) Patent No.: US 7,518,365 B2
(45) Date of Patent: Apr. 14, 2009

(54) HEAD COIL ARRANGEMENT WITH AN ADJUSTABLE NECK-ENGAGING PORTION FOR USE IN A MAGNETIC RESONANCE APPARATUS

(75) Inventor: Daniel Driemel, Öderan (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/761,541

(22) Filed: Jun. 12, 2007

(65) Prior Publication Data

US 2007/0285093 A1 Dec. 13, 2007

(30) Foreign Application Priority Data

Jun. 12, 2006 (DE) ................ 10 2006 027 190

(51) Int. Cl.
*G01V 3/00* (2006.01)

(52) U.S. Cl. ...................................... 324/318; 600/422

(58) Field of Classification Search ................. 324/318, 324/322; 600/415, 422
See application file for complete search history.

(56) References Cited

U.S. PATENT DOCUMENTS

| 5,305,750 | A | | 4/1994 | Makita |
| 5,379,768 | A | * | 1/1995 | Smalen ........................ 600/410 |
| 5,743,264 | A | * | 4/1998 | Bonutti ....................... 600/415 |
| 5,945,827 | A | | 8/1999 | Gronauer et al. |
| 6,980,002 | B1 | | 12/2005 | Petropoulos et al. |
| 2003/0020475 | A1 | | 1/2003 | Leussler |
| 2004/0186375 | A1 | | 9/2004 | Vavrek et al. |

FOREIGN PATENT DOCUMENTS

EP 1 624 314 4/2006

\* cited by examiner

*Primary Examiner*—Louis M Arana
(74) *Attorney, Agent, or Firm*—Schiff Hardin LLP

(57) ABSTRACT

Head coil arrangement for a magnetic resonance apparatus has a housing with a number of coil elements arranged in or on the housing, and the housing has at least one movable and/or moldable housing part (2*a*) for adjustment to different neck shapes in the region designated for the neck of a patient.

16 Claims, 4 Drawing Sheets

HEAD COIL ARRANGEMENT WITH AN ADJUSTABLE NECK-ENGAGING PORTION FOR USE IN A MAGNETIC RESONANCE APPARATUS

BACKGROUND OF THE INVENTION

1. Field of the Invention

The present invention relates to a head coil arrangement of the type having a housing in or on which a number of coil elements are arranged.

2. Description of the Prior Art

Head coil arrangements of this type are known and are used in magnetic resonance devices as high-frequency transmitting and receiving coils. If the coils operate in a receiving mode, the size of the coils in relation to the size of the examination subject plays a decisive role in the resulting signal-to-noise ratio. The signal-to-noise ratio is optimal if the coils rest as close as possible to the surface of the subject, in this case the head.

This is particularly critical when capturing images of regions close to the patient's neck, such as the cerebellum for example. Due to the widely varying neck shapes of different patients, for example thick necks, thin necks, short necks, long necks, etc., it is particularly difficult to achieve a suitable shape with the closest possible proximity to the patient's head.

It is known how to produce a head coil arrangement with a coil with a fixed neck shape. This is disadvantageous however, since the fixed neck shape may come into contact with the subject at a location that is too high for some patients, which may lead to pressure marks or an uncomfortable positioning of the head. On the other hand, the fixed neck shape may extend too low for other patients, leading to poor signal intensity because of the larger-than-optimal spacing that then exists. A further disadvantage of a fixed neck shape of this kind is that the position of the head within the head coil arrangement is fixed, with the result that an individual positioning of the head is not possible.

Particularly when developing new head coil arrangements with a relatively large number of individual coils, it is necessary to bring the individual coils close to the region of the body to be examined, because, due to the relatively small coils, the intensity of the receiving signal is lower and a poorer signal-to-noise ratio is thus achieved with the same spacing.

SUMMARY OF THE INVENTION

An object of the present invention is to provide a head coil arrangement that is suitable for a large number of neck shapes and has an improved signal-to-noise ratio.

This object is achieved according to the invention by a head coil arrangement of the type described above that at least one movable and/or moldable housing part is provided in the region designated for a patient's neck, allowing adjustment to different neck shapes.

In the head coil arrangement according to the invention, the shape of the housing in the region designated for the subject's neck can be modified by a user, and the housing can thus be shaped to the individual neck of the received head. Thus an improved signal intensity for each patient and therefore a better signal-to-noise ratio is achieved because the individual coils are closer to the patient's head. For an individual positioning of the head, the housing part advantageously can be lowered in such a way that when positioning the head a substantially uniform region results and the head can thus be individually positioned. If the head is in a suitable position, the movable and/or moldable housing part can be adjusted to the actual neck shape by a user.

According to the invention, a number of movable and/or moldable housing parts can be provided in the neck region in order to increase the possibilities for adjustment to different neck shapes.

The individual coils can be integrated in the housing or provided on the housing. Furthermore, it is possible to provide coils on printed circuit boards and to provide these printed circuit boards on the housing by suitable fixing elements, such as plug-in connectors for example. Preferably, 32 or more individual coils may be provided in the head coil arrangement according to the invention, thus resulting in 32 or more receiving channels.

In a particularly advantageous manner, the coil geometry can be selected so that the housing part has only complete coils that can be brought close to the head in the neck region. If there are only parts of some coils on the housing part and the associated remaining parts are situated on the rest of the housing, suitable contacting must be provided, for example by a flexible wire or sliding contact, so that the coils remain closed.

In an embodiment, the housing part is designed so it can be moved and/or bowed toward the interior of the head coil arrangement. Both an embodiment in which the housing part is fixed in terms of shape may be moved toward the neck of a patient, and an embodiment in which the housing part can change its shape and can thus be bowed, are therefore possible. The housing part is preferably in a lowered position when it is not moved or bowed toward the inside of the head coil arrangement, i.e. the local coil arrangement has a substantially uniform and flat internal surface.

Depending on position and/or shape, the housing part of the head coil arrangement according to the invention may overlap another housing part at least partially, particularly if a moldable housing part is used which nevertheless has a fixed surface. This type of overlap occurs in a lowered position for example. It may be expediently for the overlapping region of the housing part to be moved at least partially into a receiving device or holding device, which can be arranged or embodied on or in another housing part. In this case, a receiving device may be provided underneath the other housing part, for example, into which the housing part slides. This does not have to be closed, but can also form a simple holding device.

Particularly in the case of fixed-surface housing parts of this kind, which form an overlap with at least one other housing part, the housing part may expediently be guided with the aid of a linear guide on at least one side. One housing part sliding under another is thus likewise supported by a linear guide of this type.

In another embodiment of the invention, the housing part can be subject to or pre-stressed by an elastic force toward the interior of the head coil arrangement. This elastic force may be produced, for example, by the housing part itself. For this purpose, the housing part may in particular be made out of viscofoam, i.e., a viscoelastic foam. Viscofoam has a tendency to return to a certain shape. Moreover, the material is elastic and therefore can adjust to different neck shapes. Accordingly, the shape that the housing part endeavors to adopt may be a shape that is bowed toward the interior of the head coil arrangement, in other words towards the neck. For example, in order to lower the housing part, it is simply pressed outward. Alternatively, the elastic force may likewise be produced by a spring or an inflatable air cushion. The housing part is flexibly moldable in this case, and the elastic force again has the effect, for example, of bowing it inward.

Naturally a fixed-shape housing part which can be moved inward can also be subject to an elastic force of this kind.

In the embodiments making use of elastic force, a locking device can be provided to lock the housing part in place in a pre-stressed, in particular lowered, position. In the example using viscofoam, the flexible housing part is then pressed outward so that it is not bowed out of the other housing. Thus an overlap may be produced, it being possible for the housing part as described above to be introduced into a holding device or receiving device. In this receiving device a locking device, for example, a pin may be provided that interacts with an allocated recess in the housing part, or a gripping-type locking device may be used. The locking device alternatively may be a mechanical blocking device that prevents the housing part from bowing toward the interior of the head coil arrangement, such as a locking pin for example. In this case, the patient is first positioned individually inside the head coil arrangement. Subsequently, the locking device, if necessary by means of a suitable actuator, is released by an operator and the housing part automatically adjusts to the shape of the neck due to the elastic force. In this connection, dampers may also be provided to prevent the released housing part from moving too quickly.

In addition or in an alternative embodiment, the housing part can be moved or molded by an actuating arrangement. There are various design options for an actuating arrangement for this purpose.

The actuating arrangement may include a rotating cam that engages the housing part. The cam may be substantially bead-shaped so that different degrees of bowing result in different cam positions. This type of cam may, for example, be rotated by an actuator, notably by a hand wheel.

Alternatively, a slide, preferably one that engages a region of the housing part guided by the linear guide, may be provided as an actuating arrangement. In this case, the housing part is displaced in the linear guide by the slide, with the result that the housing part adopts a different position and/or shape.

In addition to a fully flexible housing part, the housing part may have at least two particularly rigid housing sections connected by a joint. In this embodiment, the housing sections do not have to be flexible themselves because the joint already allows moldability. A housing part of this kind may, for example, allow triangular-type bowing. Naturally, it is also possible for more than two housing sections to be provided, which are connected by joints in order to achieve a more precise adjustment to shape.

In order to enhance the patient's comfort, a pressure damper may be provided on the inside of the housing part, such as a cushion. The housing part that is usually designed somewhat firmer, then does not exert any direct pressure on the patient's head during shaping, as the patient is advantageously cushioned by the pressure damper in such a way that, in spite of its proximity with the coils, the head is comfortably positioned.

DESCRIPTION OF THE PREFERRED EMBODIMENTS

Several exemplary embodiments of a head coil arrangement according to the invention are shown below. All the same components in the various drawings have the same reference numbers.

Figure 1:
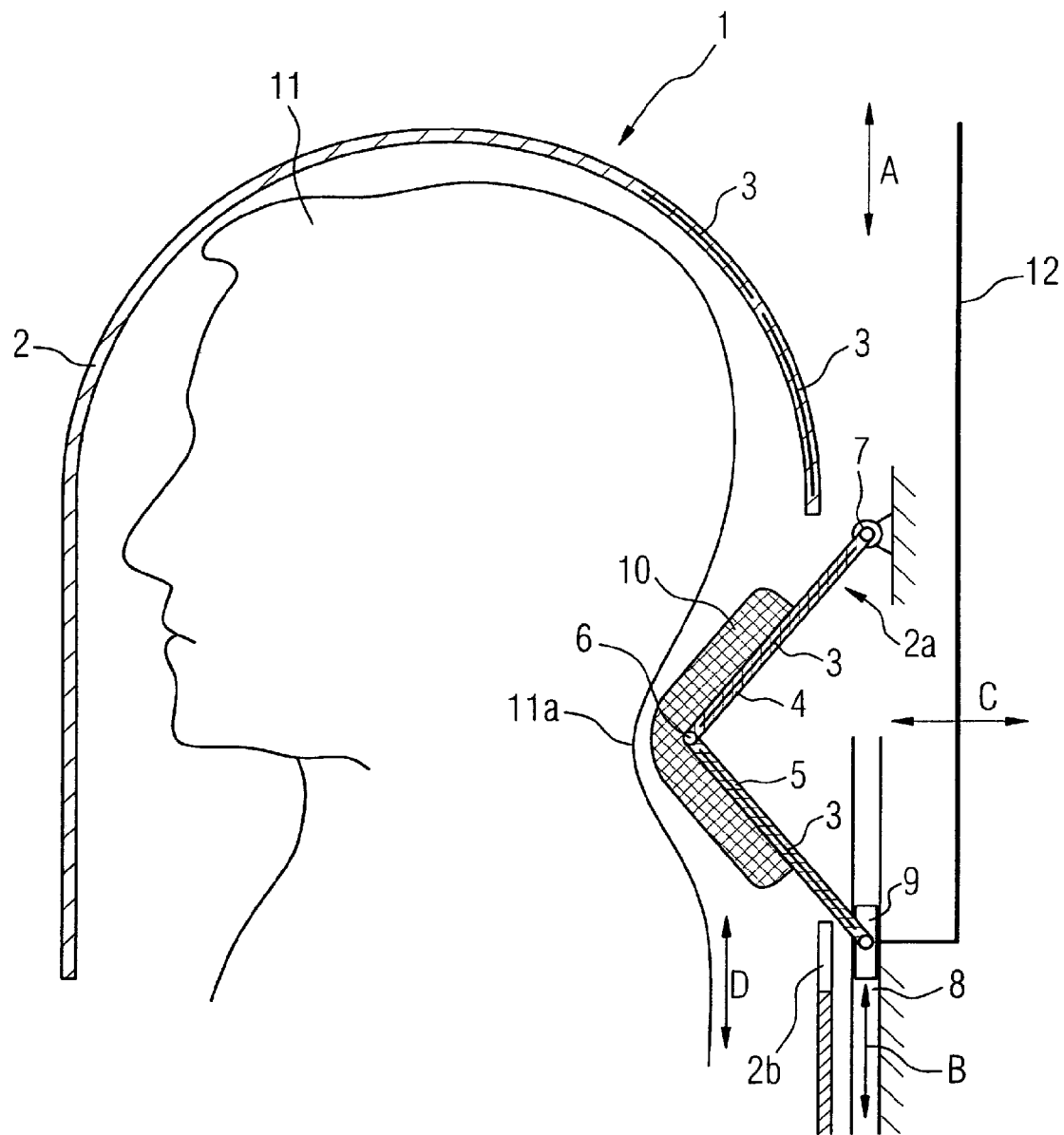
FIG. 1 shows a vertical section through a head coil arrangement according to the invention in a first exemplary embodiment.

FIG. 1 shows a head coil arrangement 1 according to a first exemplary embodiment. This arrangement has a housing 2 in which the individual coils 3 are arranged, of which only some are illustrated in outlines. For clarity, the individual coils are not illustrated in the other drawings, but these coils are of course present in every exemplary embodiment. The coils 3 do not have to be arranged within the housing 2. They may also be provided or arranged on the housing 2. In the region designated for the patient's neck, a movable, moldable housing part 2a is provided. The housing part 2a is formed by housing sections 4 and 5 that are connected so as to allow them to swivel toward each other by means of a joint 6. On one side, the housing section 4 is positioned so that it can be swiveled by means of another joint 7. The housing section 5 of housing part 2a is guided in a linear guide 8 by means of a sliding carriage 9. The linear guide 8 at the same time forms a recess for the housing section 5 of the housing part 2a, should this need to be moved into a lowered position. The linear guide 8 is arranged underneath another housing part 2b and secured to the latter. Furthermore, the housing part 2a has a cushion 10 which allows a patient's head 11 only shown schematically to be comfortably supported in the neck region.

The sliding carriage 9 is connected to a schematically shown slide 12 which is positioned so that it can move, as is indicated by arrow A.

If the slide is moved along arrow A, the sliding carriage 9 moves along arrow B in the linear guide 8. As a result the housing part 2a changes its shape and position when the housing sections 4 and 5 are moved and joints 6 and 7 are swiveled, as is indicated by arrow C. If the sliding carriage 9 moves to the far left in the linear guide 8, the housing part 2a will become flat and will be in a lowered position in which it will not jut out into the inside of the head coil arrangement 1. In this position, the patient's head 11 can be positioned individually without obstacles in the head coil arrangement 1, as is indicated by arrow D. Once the head 11 is positioned, with the aid of the slide an operator may adjust the position and shape of the housing part 2a optimally to the shape of the neck 11a of the head 11.

Figure 2:
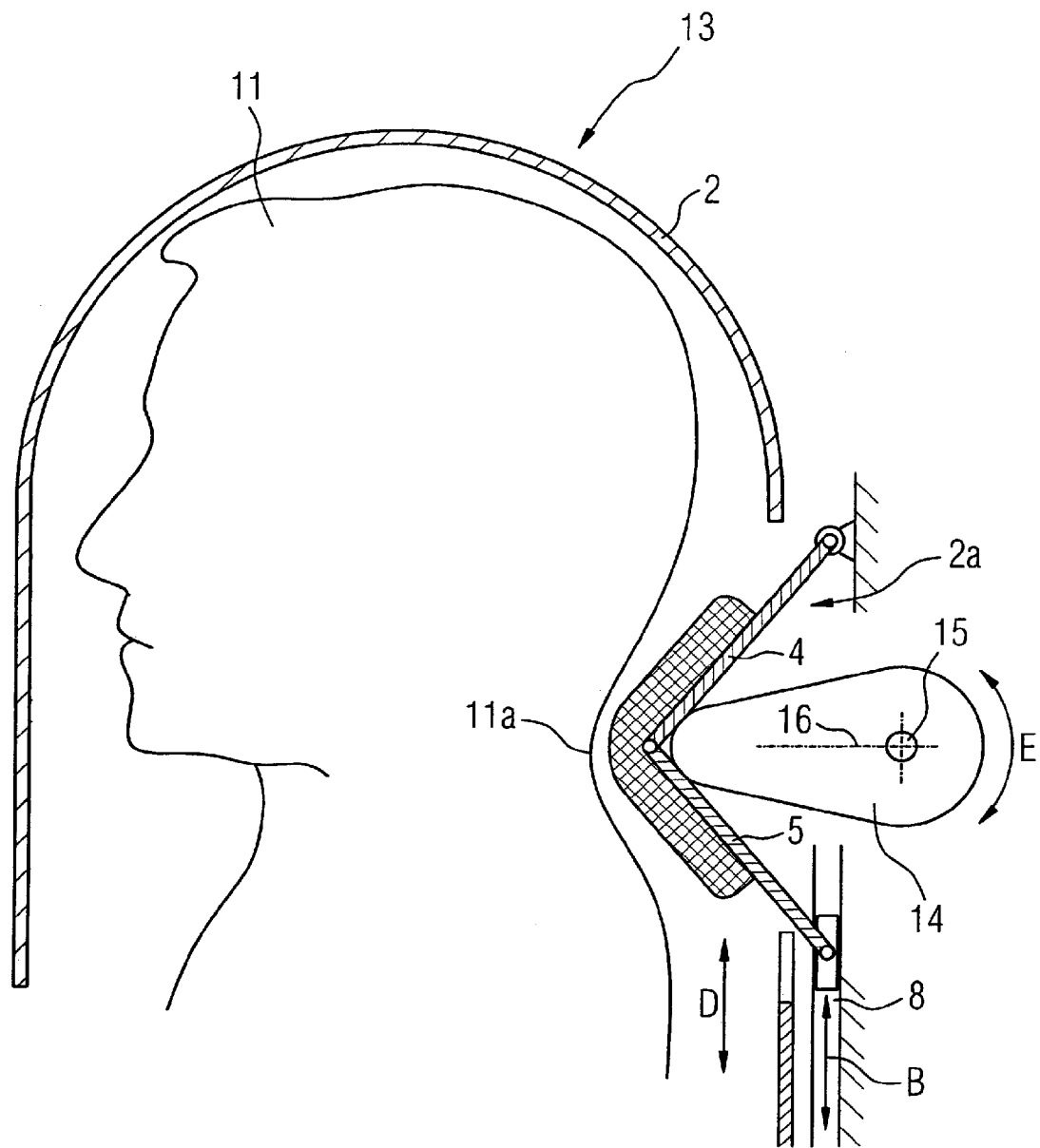
FIG. 2 shows a vertical section through a head coil arrangement according to the invention in a second exemplary embodiment.

FIG. 2 shows a second exemplary embodiment of a head coil arrangement 13, which as part of the housing 2 again has a housing part 2a formed by two housing sections 4, 5, and is positioned on one side in a linear guide 8. As an actuating element to mold or move the housing part 2a, a cam 14 is however provided in this case which, as is indicated by arrow E, can be rotated around an axis 15. The cam 14 can be rotated by an operator by means of a hand wheel not shown in detail. If the longitudinal axis 16 of the cam 14 is aligned in a horizontal direction, the housing part 2a is in the lowered position. In this case it is again possible to position a head 11 individually, arrow D. By rotating the cam 14, the shape and position of the housing part 2a can be adjusted to the neck 11a of head 11, which is made possible by positioning one side of the housing part 2a in the linear guide 8, arrow B.

Figure 3:
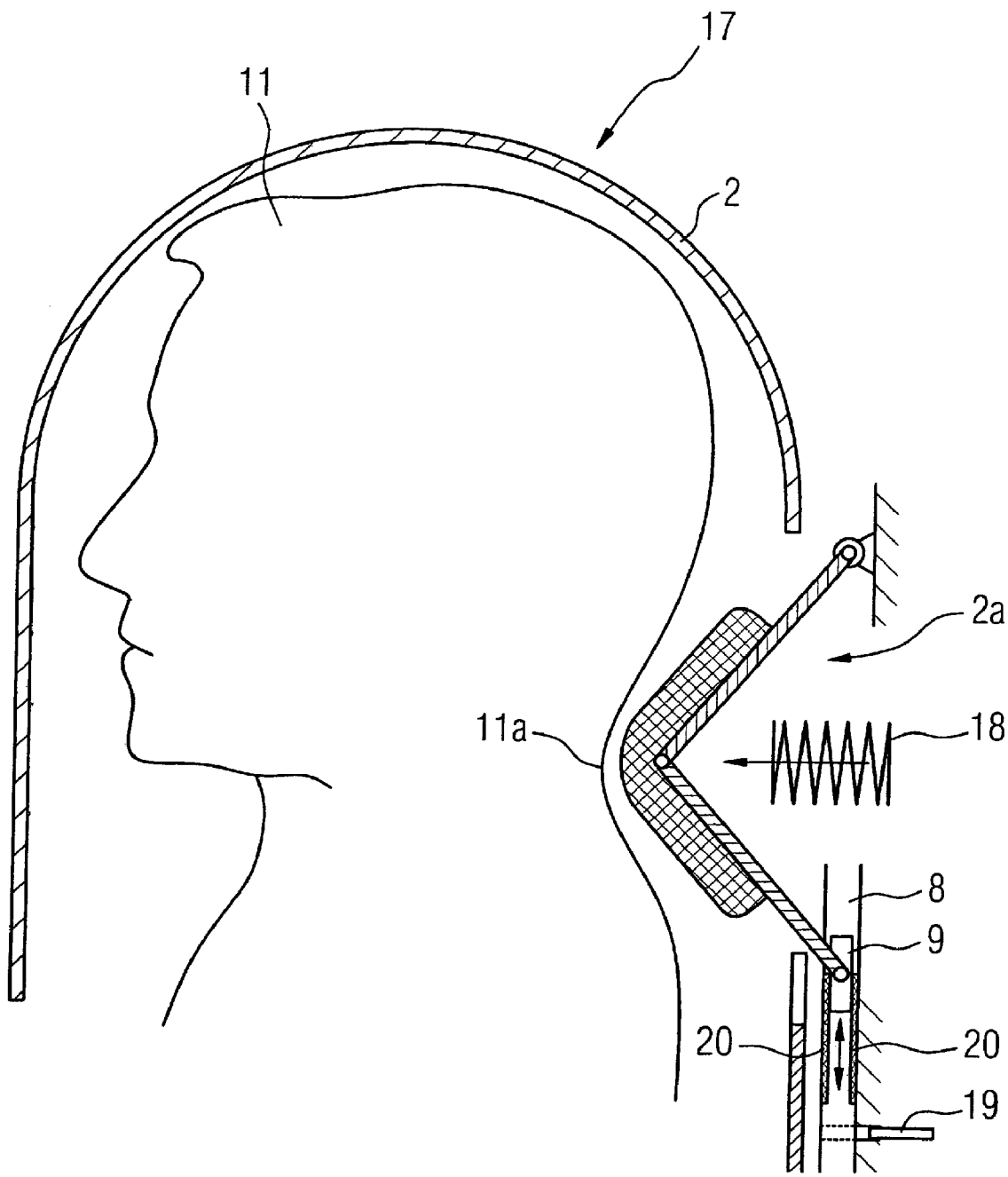
FIG. 3 shows a vertical section through a head coil arrangement according to the invention in a third exemplary embodiment.

Another head coil arrangement 17 with a movable and moldable housing part 2a of the housing 2 is shown in FIG. 3.

In this case, the housing part 2a is pre-stressed in the direction of the inside of the head coil arrangement 17 by means of the elastic force of a spring 18. Instead of spring 18, an air bellows or a viscoelastic material, for example, may be used. For individual positioning of a head 11, the housing part 2a is pushed into the lowered position against the force of the spring 18, whereby the sliding carriage 9 moves to the left in the linear guide 8. There a locking device 19 is provided in the form of a pin, with which the housing part 2a is held in the lowered position. After the head has been positioned, the housing part 2a is released by releasing the locking device 19. Subsequently, the housing part 2a automatically adjusts to the neck 11a of the positioned head 11 as a result of the elastic force of the spring 18. So that the housing part 2a does not spring back on the head 11 too fast, dampers 20 are provided in the linear guide 8 which slows down the movement of the housing part 2a.

Although a housing part 2a formed of two rigid housing sections 4 and 5 connected by a joint 6 was described in each of the exemplary embodiments of FIGS. 1 to 3, another embodiment of the housing part 2a is conceivable. Thus sections 4 and 5 may themselves have a certain flexibility, or the whole housing part 2a may be formed of only one section which is flexibly designed as a whole. A design with more than two sections and more than one joint is likewise conceivable. The length of the housing sections 4, 5 also can be adjusted according to requirements. Moreover, a linear guide may be provided on both sides. Furthermore, guiding on the side in the overlap region does not have to be by means of a linear guide. Sliding fixtures, rolling fixtures or the like, for example, are also conceivable.

Figure 4:
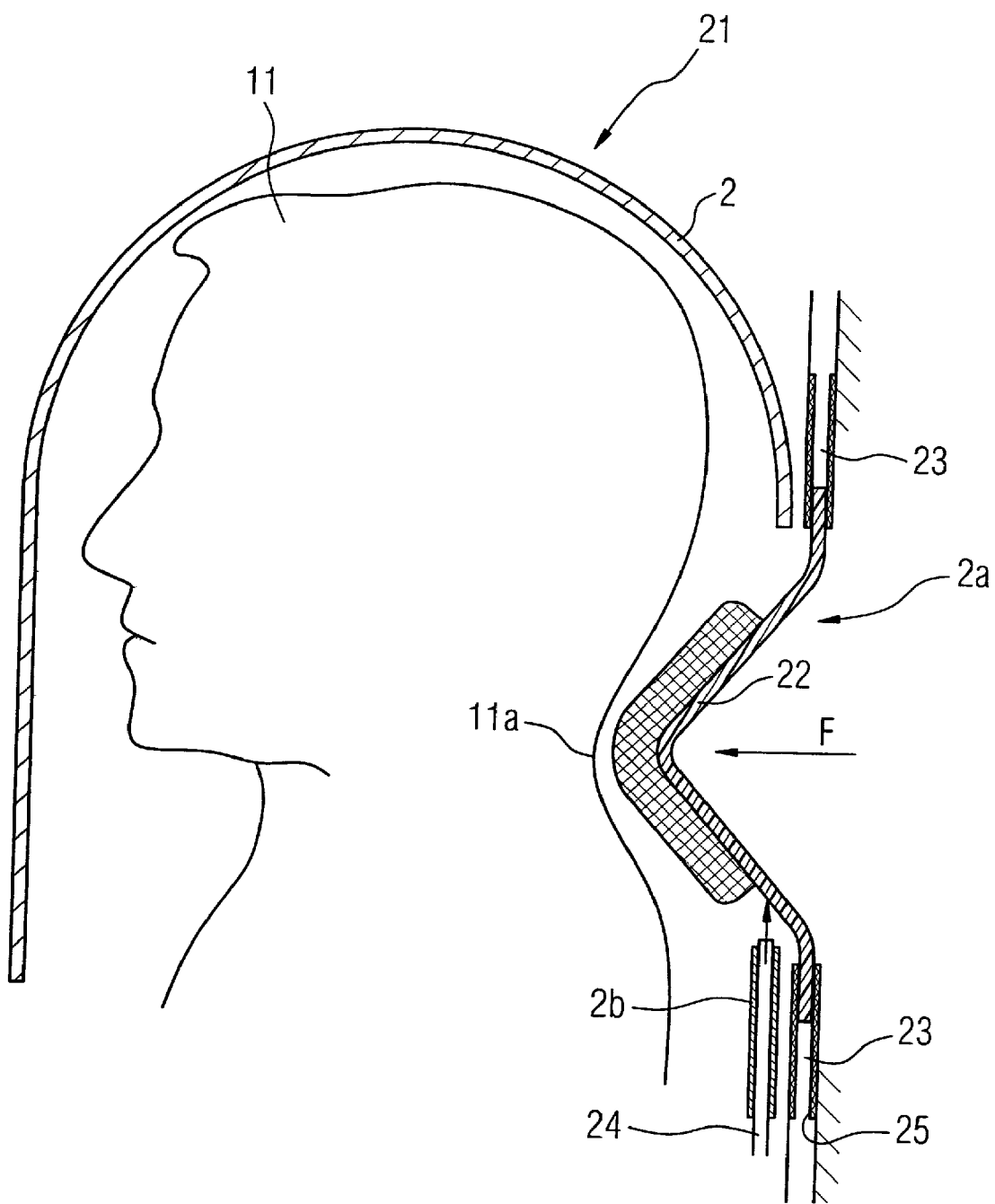
FIG. 4 shows a vertical section through a head coil arrangement according to the invention in a fourth exemplary embodiment.

FIG. 4 shows a fourth exemplary embodiment of a head coil arrangement 21. Here the housing part 2a of the housing 2 consists of a viscofoam 22 which is pre-stressed in a certain bowed position, as is indicated by arrow F. The housing part 23 is guided in sliding guides 23 on both sides. In another housing part 2b, a retractable rod 24 is positioned that serves as a locking device. If the viscofoam 22 is pushed into the lowered position, the rod 24 can be retracted so that the housing part 2a remains in the lowered position. Naturally, other locking options are also conceivable. Then a patient's head 11 can again be individually positioned. If the locking device is released, the pre-stressed viscofoam 22 automatically adjusts to the neck contour 11a of the head 11. So that this does not occur too quickly, dampers 25 are once again provided in the sliding guides 23, which dampen the movement of the housing part 2a sufficiently.

Although only one housing part 2a is shown in the exemplary embodiments, a number of such movable and/or moldable housing parts can be provided for adjusting the housing to different neck shapes.

Although modifications and changes may be suggested by those skilled in the art, it is the intention of the inventor to embody within the patent warranted hereon all changes and modifications as reasonably and properly come within the scope of his contribution to the art.

I claim:

1. A head coil arrangement for use in a magnetic resonance apparatus, comprising:
   a housing comprising a first housing portion configured to generally conform to and encompass a human head of a subject except behind the neck of the subject;
   a plurality of magnetic resonance coil elements carried by said housing; and
   said housing comprising a second housing portion that is situated in a region of the neck of the subject when the first housing portion is placed on the head of the subject, said second housing portion comprising a housing part that is movable or deformable and a linear guide disposed on at least one side of said housing part engaging said linear guide and, said housing part being guided at said at least one side in said linear guide to adjust said housing part to different neck shapes.

2. A head coil arrangement as claimed in claim 1 wherein said first housing portion has an interior in which the head of the subject is received, and wherein said housing part is movable or deformable toward said interior of said housing.

3. A head coil arrangement as claimed in claim 1 wherein said first housing portion comprises a further housing part adjacent to said housing part that is movable or deformable, and said housing part that is movable or deformable, upon being moved or deformed, being configured to overlap said adjacent further housing part.

4. A head coil arrangement as claimed in claim 3 wherein said housing part that is movable or deformable overlaps said adjacent further housing part in an overlapping region, and wherein said adjacent housing part comprises a receptacle within which said housing part that is movable or deformable is moved or deformed.

5. A head coil arrangement as claimed in claim 1 wherein said first housing portion comprises an interior in which the head of the subject is received, and wherein said head coil arrangement comprises an elastic force source that interacts with said housing part to exert an elastic force on said housing part to urge said housing part toward said interior of said housing.

6. A head coil arrangement as claimed in claim 5 wherein said housing part is comprised of viscofoam, that forms said elastic force source.

7. A head coil arrangement as claimed in claim 5 wherein said elastic force source is selected from the group consisting of mechanical springs and inflatable/deflatable air bellows.

8. A head coil arrangement as claimed in claim 5 comprising a locking device that interacts with said housing part to hold said housing part in place after said elastic force has been applied to said housing part.

9. A head coil arrangement as claimed in claim 1 comprising an actuator that mechanically interacts with said housing part to move or deform said housing part.

10. A head coil arrangement as claimed in claim 9 wherein said actuator comprises a rotating cam that engages said housing part.

11. A head coil arrangement as claimed in claim 10 comprising a crank connected to said rotating cam to rotate said cam.

12. A head coil arrangement as claimed in claim 9 wherein said actuator comprises a slider connected to a portion of said housing part, said slider sliding in said linear guide in which said slider slides.

13. A head coil arrangement as claimed in claim 1 wherein said housing part comprises at least two rigid housing part sections connected with each other by a joint.

14. A head coil arrangement as claimed in claim 1 wherein said housing part has a side configured to face toward the neck of the examination subject, and wherein said head coil arrangement comprises a pressure damper mounted at said side of said housing part.

15. A head coil arrangement as claimed in claim 14 wherein said pressure damper is a cushion.

16. A head coil arrangement as claimed in claim 1 wherein said housing part carries at least one of said plurality of magnetic resonance coil elements.

* * * * *